US006902552B2

United States Patent
VanGompel et al.

(10) Patent No.: US 6,902,552 B2
(45) Date of Patent: *Jun. 7, 2005

(54) CURVED SANITARY NAPKIN WITH GARMENT ATTACHMENT PANELS

(75) Inventors: Paul Theodore VanGompel, Hortonville, WI (US); Julie Terese Brocker, Appleton, WI (US); Lori Sue Schutkoske, Winneconne, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/407,403

(22) Filed: Apr. 4, 2003

(65) Prior Publication Data

US 2003/0195488 A1 Oct. 16, 2003

Related U.S. Application Data

(62) Division of application No. 08/892,744, filed on Jul. 15, 1997, now abandoned, which is a continuation of application No. 07/954,102, filed on Sep. 30, 1992, now abandoned.

(51) Int. Cl.$^7$ ............................ A61F 13/15; A61F 13/20
(52) U.S. Cl. .................. 604/385.04; 604/387; 604/391
(58) Field of Search ....................... 604/385.03, 385.05, 604/387, 355.22–355.29

(56) References Cited

U.S. PATENT DOCUMENTS

| 75,434 | A | 3/1868 | Libbey |
| 462,974 | A | 11/1891 | Allen |
| 478,053 | A | 6/1892 | Dyer |
| 791,354 | A | 5/1905 | Merkley |
| 830,757 | A | 9/1906 | Williams |
| 867,091 | A | 9/1907 | Altermatt |
| 924,337 | A | 6/1909 | Frommann |
| 1,022,894 | A | 4/1912 | Sprague |
| 1,146,245 | A | 7/1915 | Goldman |
| 1,386,936 | A | 8/1921 | Kirwan |

(Continued)

FOREIGN PATENT DOCUMENTS

| AU | 412412 | 1/1968 |
| AU | 30274/84 | 9/1985 |

(Continued)

OTHER PUBLICATIONS

Takatoshi Kobayashi, Utilization of water–absorbent polymers in hygienic field; *Zairyo Gijutsu*, 6 (9), 361–365 (1988) (in Japanese, with translation).

(Continued)

*Primary Examiner*—Karin Reichle
(74) *Attorney, Agent, or Firm*—Brinks Hofer Gilson & Lione

(57) ABSTRACT

An elongated, curved sanitary napkin having elasticized, raised side edges along the opposite sides of an absorbent. A garment attachment panel is secured to the underside of each side edge. A fixed portion of the garment attachment panel is bonded to each side edge so that a free portion of each of the garment attachment panels, extending from the fixed portion, is directed generally inward and downward. During use, the garment attachment panels are fastened together beneath an undergarment crotch. The fastener and the garment attachment panels are dimensioned so that, when fastened, the garment attachment panels exert a pull on the side edges and control their deflection, thereby preventing them from folding in over the absorbent. The garment attachment panels confine the crotch portion of the undergarment under the absorbent so that the edges of the panty crotch are prevented from pulling up and onto the absorbent.

11 Claims, 3 Drawing Sheets

U.S. PATENT DOCUMENTS

| | | |
|---|---|---|
| 1,653,857 A | 12/1927 | Kelly |
| 1,664,298 A | 3/1928 | Katz |
| 1,837,483 A | 12/1931 | Cecil-Reaney |
| 1,882,309 A | 10/1932 | Williams |
| 1,912,783 A | 6/1933 | Meyer |
| RE18,939 E | 9/1933 | Harrington |
| 1,975,457 A | 10/1934 | Heyman |
| 1,975,618 A | 10/1934 | Raskin |
| 2,026,158 A | 12/1935 | Bennett |
| 2,076,526 A | 4/1937 | Brown |
| 2,154,332 A | 4/1939 | Hirsch |
| 2,295,016 A | 9/1942 | Scribner |
| 2,408,508 A | 10/1946 | Canavan |
| 2,636,494 A | 4/1953 | Hon |
| 2,787,271 A | 4/1957 | Clark |
| 2,840,078 A | 6/1958 | Smith |
| 2,890,701 A | 6/1959 | Weinman |
| 3,070,095 A | 12/1962 | Torr |
| 3,096,765 A | 7/1963 | Cornwell |
| 3,315,677 A | 4/1967 | Tyrrell, Jr. |
| 3,342,184 A | 9/1967 | Joa |
| 3,397,697 A | 8/1968 | Rickard |
| 3,400,718 A | 9/1968 | Saijo |
| 3,613,686 A | 10/1971 | Woskin |
| 3,670,731 A | 6/1972 | Harmon |
| 3,686,024 A | 8/1972 | Nankee et al. |
| 3,744,494 A | 7/1973 | Marsan |
| 3,881,490 A | 5/1975 | Whitehead et al. |
| 3,888,255 A | 6/1975 | Shah et al. |
| 3,890,974 A | 6/1975 | Kozak |
| 3,897,783 A | 8/1975 | Ginocchio |
| 3,913,580 A | 10/1975 | Ginocchio |
| 3,973,567 A | 8/1976 | Srinivasan et al. |
| 4,041,203 A | 8/1977 | Brock et al. |
| 4,055,180 A | 10/1977 | Karami |
| 4,055,184 A | 10/1977 | Karami |
| D247,372 S | 2/1978 | Whitehead |
| 4,144,886 A | 3/1979 | Holst et al. |
| 4,147,580 A | 4/1979 | Buell |
| 4,176,667 A | 12/1979 | Herring |
| 4,217,901 A | 8/1980 | Bradstreet et al. |
| 4,248,822 A | 2/1981 | Schmidt |
| 4,280,978 A | 7/1981 | Dannheim et al. |
| 4,285,343 A | 8/1981 | McNair |
| 4,324,246 A | 4/1982 | Mullane et al. |
| 4,327,732 A | 5/1982 | Thinnes |
| 4,333,465 A | 6/1982 | Wiegner |
| 4,342,314 A | 8/1982 | Radel et al. |
| 4,364,992 A | 12/1982 | Ito et al. |
| 4,425,130 A | 1/1984 | DesMarais |
| 4,456,570 A | 6/1984 | Thomas et al. |
| 4,463,045 A | 7/1984 | Ahr et al. |
| 4,496,359 A | 1/1985 | Pigneul |
| 4,500,585 A | 2/1985 | Erickson |
| 4,540,415 A | 9/1985 | Korpman |
| 4,551,143 A | 11/1985 | Cook et al. |
| 4,589,876 A | 5/1986 | Van Tilburg |
| 4,608,047 A | 8/1986 | Mattingly |
| 4,655,759 A | 4/1987 | Romans-Hess et al. |
| 4,668,230 A | 5/1987 | Damico et al. |
| 4,687,478 A | 8/1987 | Van Tilburg |
| 4,701,177 A | 10/1987 | Ellis et al. |
| 4,701,178 A | 10/1987 | Glaug et al. |
| 4,710,186 A | 12/1987 | DeRossett et al. |
| RE32,649 E | 4/1988 | Brandt et al. |
| 4,738,676 A | 4/1988 | Osborn, III |
| 4,755,413 A | 7/1988 | Morris |
| 4,759,754 A | 7/1988 | Korpman |
| 4,770,657 A | 9/1988 | Ellis et al. |
| 4,773,905 A | 9/1988 | Molee et al. |
| 4,790,838 A | 12/1988 | Pigneul et al. |
| 4,798,601 A | 1/1989 | Shirose et al. |
| 4,798,603 A | 1/1989 | Meyer et al. |
| 4,798,604 A | 1/1989 | Carter |
| 4,848,572 A | 7/1989 | Herrera |
| 4,862,574 A | 9/1989 | Seidy |
| 4,886,513 A | 12/1989 | Mason, Jr. et al. |
| 4,900,319 A | 2/1990 | Richwine |
| 4,900,320 A | 2/1990 | McCoy |
| 4,911,701 A | 3/1990 | Mavinkurve |
| 4,917,697 A | 4/1990 | Osborn, III et al. |
| 4,936,839 A | 6/1990 | Molee et al. |
| 4,940,462 A | 7/1990 | Salerno |
| 4,964,860 A | 10/1990 | Gipson et al. |
| 5,007,906 A | 4/1991 | Osborn, III et al. |
| 5,074,856 A | 12/1991 | Coe et al. |
| 5,092,860 A | 3/1992 | Pigneul |
| 5,113,705 A | 5/1992 | Nakanishi et al. |
| 5,125,918 A | 6/1992 | Seidy |
| 5,133,704 A | 7/1992 | Wheeler |
| 5,176,671 A | 1/1993 | Roessler et al. |
| 5,201,727 A | 4/1993 | Nakanishi et al. |
| 5,221,275 A | 6/1993 | Van Iten |
| 5,275,591 A | 1/1994 | Mavinkurve |
| 5,346,486 A | 9/1994 | Osborn, III et al. |
| 5,354,400 A | 10/1994 | Lavash et al. |
| 5,389,094 A | 2/1995 | Lavash et al. |
| 5,391,162 A | 2/1995 | Widlund et al. |
| 5,447,507 A | 9/1995 | Yamamoto |
| 5,478,336 A | 12/1995 | Pigneul |
| 5,489,283 A | 2/1996 | Van Tillburg |
| 5,520,676 A | 5/1996 | Lavash et al. |
| 5,578,026 A | 11/1996 | Lavash et al. |
| 5,620,430 A | 4/1997 | Bamber |
| 6,231,554 B1 | 5/2001 | Menard |
| 6,387,084 B1 | 5/2002 | VanGompel et al. |

FOREIGN PATENT DOCUMENTS

| | | |
|---|---|---|
| AU | 579829 | 9/1986 |
| AU | 74156/87 | 12/1987 |
| AU | 19066/88 | 1/1989 |
| AU | 20013/88 | 1/1989 |
| AU | 19726/88 | 3/1989 |
| AU | 21579/88 | 3/1989 |
| AU | 41709/89 | 3/1989 |
| AU | 32242/89 | 10/1989 |
| AU | 32764/89 | 10/1989 |
| AU | 36006/89 | 12/1989 |
| AU | 41141/89 | 3/1990 |
| AU | 51464/90 | 9/1990 |
| AU | 594536 | 6/1998 |
| AU | 12086/88 | 8/1998 |
| CA | 2023577 | 2/1992 |
| DE | 1491234 | 4/1969 |
| DE | 3319421 | 11/1984 |
| EP | 0091412 | 10/1983 |
| EP | 0127103 | 12/1984 |
| EP | 0130848 | 1/1985 |
| EP | 0155515 | 9/1985 |
| EP | 0280998 | 9/1988 |
| EP | 0345703 | 12/1988 |
| EP | 0301491 | 2/1989 |
| EP | 0304644 | 3/1989 |
| EP | 0314535 | 5/1989 |
| EP | 0330206 | 8/1989 |
| EP | 0331018 | 9/1989 |
| EP | 0334644 | 9/1989 |
| EP | 0337438 | 10/1989 |
| EP | 0347319 | 12/1989 |
| EP | 0409307 | 1/1990 |
| EP | 0359501 | 3/1990 |

| EP | 0360285 | 3/1990 |
| EP | 0360680 | 3/1990 |
| EP | 0426235 | 5/1991 |
| EP | 0581258 | 2/1994 |
| FR | 2586558 | 3/1987 |
| GB | 2048684 | 12/1980 |
| GB | 2161384 | 1/1986 |
| JP | 40-36391 | 12/1965 |
| JP | 46-12554 | 5/1971 |
| JP | 48-43500 | 6/1973 |
| JP | 48-59395 | 7/1973 |
| JP | 48-73497 | 9/1973 |
| JP | 49-18398 | 2/1974 |
| JP | 49-25294 | 3/1974 |
| JP | 50-10718 | 4/1975 |
| JP | 50-100399 | 8/1975 |
| JP | 50-44720 | 12/1975 |
| JP | 52-117394 | 9/1977 |
| JP | 54-154696 | 10/1979 |
| JP | 55-16135 | 2/1980 |
| JP | 57-20172 | 4/1982 |
| JP | 59-225058 | 12/1984 |
| JP | 60-75058 | 4/1985 |
| JP | 60-158828 | 10/1985 |
| JP | 60-199446 | 10/1985 |
| JP | 61-51810 | 4/1986 |
| JP | 61-154931 | 9/1986 |
| JP | 63-186645 | 8/1988 |
| JP | 04009154 A * | 1/1992 ........... A61F/13/56 |
| JP | 4-126145 | 4/1992 |
| JP | 4-364844 | 12/1992 |
| JP | 5-137750 | 6/1993 |
| JP | 5-220191 | 8/1993 |
| JP | 5-220192 | 8/1993 |
| JP | 5-269169 | 10/1993 |
| JP | 5-93429 | 12/1993 |
| JP | 5-93430 | 12/1993 |
| JP | 5-337152 | 12/1993 |
| JP | 6-047072 | 2/1994 |
| JP | 63-3858 | 1/1998 |
| WO | 92/07536 | 5/1992 |
| WO | 9207537 | 5/1992 |

OTHER PUBLICATIONS

Exhibit 1: Notice of Opposition of McNeil–PPC, Inc., ("Opponent I") to the grant of European Patent 0,590,675 / 93 115848.9, filed (Feb. 26, 1998).

Exhibit 2: Notice of Opposition of SCA Mölnlycke AB ("Opponent II"), to the grant of European Patent 0,590,675 / 93 115848.9, filed (Mar. 2, 1998).

Exhibit 3: Notice of Opposition of Paul Hartmann AG ("Opponent III"?), to the grant of European Patent 0,590,675 / 93 115848.9, filed (Feb. 23, 1998) (in German, no translation).

Exhibit 4: Response to the Office Action of Mar. 23, 1998, communicating Notices of Opposition of McNeil–PPC, Inc.; SCA Mölnlycke AB; and Paul Hartmann AG, to the grant of European Patent 0,590,675 / 93 115,848.9, filed Oct. 1, 1998.

Exhibit 5: Observations of the Opposition Division of the EPO regarding the Oppositions to the grant of European Patent 0,590,675 / 93 115,848.9, dated (Mar. 22, 1999).

Exhibit 6: Minutes of the oral proceedings before the Opposition Division on (May 3, 2000) regarding the Oppositions to the grant of European Patent 0,590,675 / 93 115,848.9.

Exhibit 7: Interlocutory Decision of the Opposition Division of the EPO regarding the Oppositions to the grant of European Patent 0,590,675 / 93 115,848.9, maintaining the Patent with amended claims, dated (Jul. 19, 2000).

Exhibit 8: Grounds of Appeal of EPO Decision of Jul. 5, 2000 on the Oppositions to European Patent No. EP–B–595, 047 filed Nov. 17, 2000 by SCA Mölnlycke AB (Opponent II).

Exhibit 9: Grounds of Appeal of EPO Decision of Jul. 5, 2000 on the Oppositions to European Patent No. EP–B–595, 047 filed Nov. 17, 2000 by SCA Mölnlycke AB (Opponent I).

Exhibit 10: Response by Patentee to Grounds of Appeal of EPO Decision of Jul. 5, 2000, on the Oppositions to European Patent No. EP–B–595,047 by Opponents I and II, filed May 23, 2001.

Exhibit 11: Summons to Attend Oral Proceedings on Jun. 16, 2003, on the Oppositions to European Patent No. 595,047, with preliminary assessment, mailed Apr. 2, 2003, by EPO.

Exhibit 12: Notice of Opposition of McNeil–PPC, Inc., to the grant of European Patent 0,595,047 / 93 115757.2, filed Jan. 30, 1998.

Exhibit 13: Notice of Opposition of SCA Mölnlycke AB, to the grant of European Patent 0,595,047 / 93 115757.2, filed Feb. 2, 1998.

Exhibit 14: Response to the Office Action of Apr. 16, 1998, communicating Notices of Opposition of McNeil–PPC, Inc. and SCA Mölnlycke AB, to the grant of European Patent 0,595,047 / 93 115757.2, filed Aug. 20, 1998.

Exhibit 15: Reply of McNeil–PPC, Inc., to the Response to the Office Action communicating Notices of Opposition of McNeil–PPC, Inc. and SCA Mölnlycke AB, to the grant of European Patent 0,595,047 / 93 115,757.2, filed Jan. 13, 1999.

Exhibit 16: Reply of SCA Mölnlycke AB, to the Response to the Office Action communicating Notices of Opposition of McNeil–PPC, Inc. and SCA Mölnlycke AB, to the grant of European Patent 0,595,047 / 93 115,757.2, filed Jan. 15, 1999.

Exhibit 17: Summons to attend oral proceedings, with observations by the Opposition Division, dated (Dec. 1, 1999).

Exhibit 18: Submission by Patentee, with amended claims and auxiliary request, filed Mar. 31, 2000.

Exhibit 19: Minutes of the oral proceedings before the Opposition Division on (May 4, 2000) regarding the Oppositions to the grant of European Patent 0,595,047 / 93 115,757.2.

Exhibit 20: European Patent Office Decision dated (Jul. 5, 2000) on the Oppositions to European Patent No. EP–B–595,047.

Decision of the Technical Board of Appeal in the Opposition to the grant of EP 590,675, dated (Sep. 3, 2003).

* cited by examiner

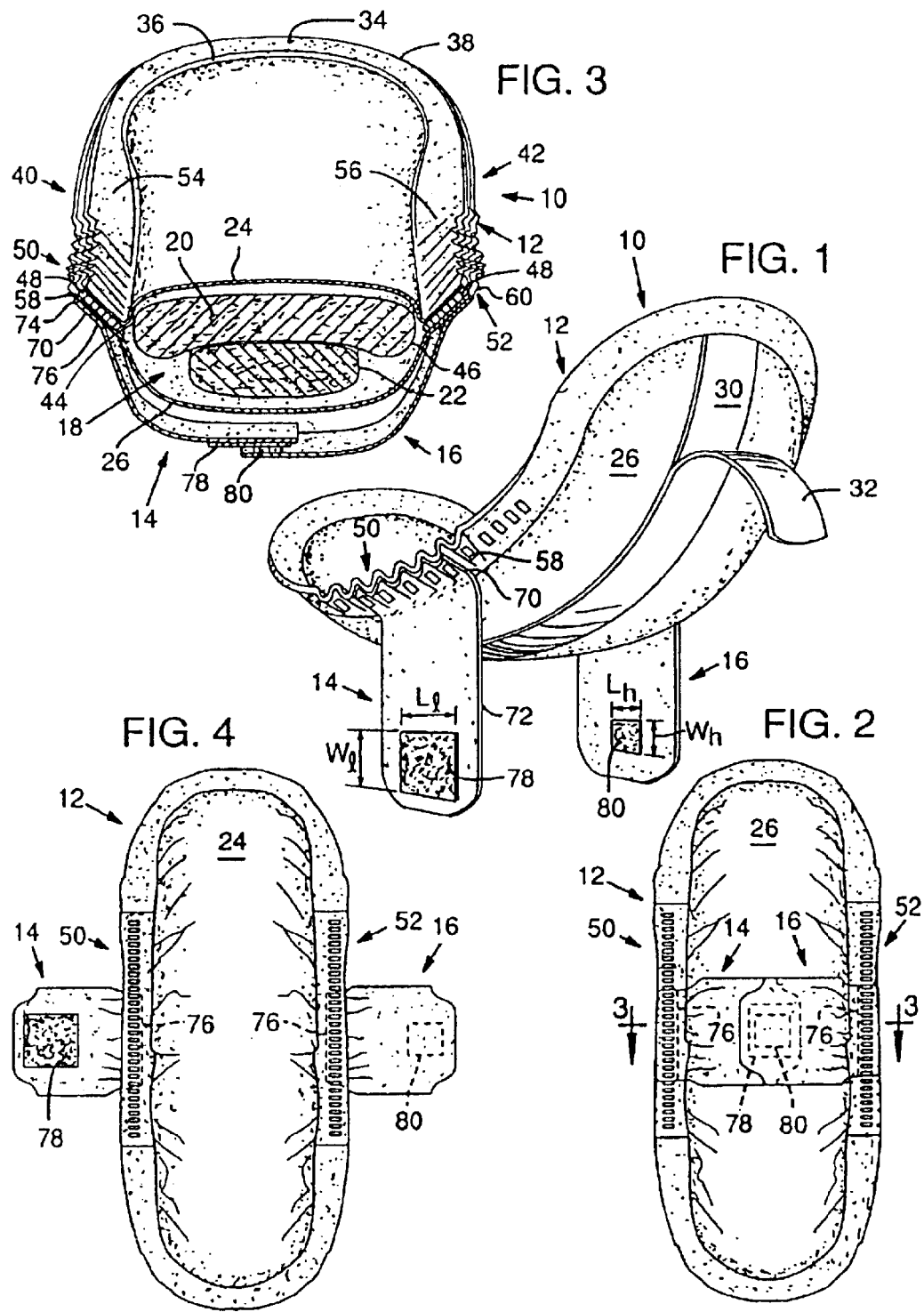

CURVED SANITARY NAPKIN WITH GARMENT ATTACHMENT PANELS

CROSS-REFERENCE TO RELATED APPLICATIONS

This is a division of application Ser. No. 08/892,744, filed Jul. 15, 1997, and now abandoned, which is a continuation of application Ser. No. 07/954,102, filed Sep. 30, 1992, and now abandoned, both of which are hereby incorporated by reference herein.

FIELD OF THE INVENTION

This invention relates to sanitary napkins and, more particularly, an elongated napkin, upwardly curved along its length with deflectable, functional side edges along its longitudinal sides, and a pair of depending garment attachment panels which, in use, may be used to control the deflection or configuration assumed by the side edges.

BACKGROUND OF THE INVENTION

The basic form of sanitary napkin, upon which the present invention is an improvement, is well known. It is referred to variously as a curved, or three dimensional, or shaped product, usually with elasticized edges. In use, it is mounted on the crotch portion of an undergarment such as a panty and, for convenience in description, the working environment of the invention will be assumed to be in a panty as worn by a female. However, the inventive concept may also be applied to infant care and adult incontinent garments.

Essentials of the existing product are an absorbent element enclosed between a bodyside permeable cover and a garment side impermeable baffle. The cover and baffle extend laterally beyond the absorbent element, at least along its longitudinal sides, and are bonded together to form a "side edge." Typically, at least longitudinally central portions of these side edges are gathered, or elasticized, tending to raise the side edges relative to the absorbent element so that the free form of the product is upwardly curved and somewhat cup shaped. Examples of this type of sanitary napkin are those sold by the Kimberly-Clark Corporation under the name Kotex® Natural Curved Maxi. Variations of the form and typical construction details are disclosed by Ellis et al. in U.S. Pat. Nos. 4,701,177 and 4,770,657, and Coe et al. in U.S. Pat. No. 5,074,856, all three assigned to Kimberly-Clark Corporation.

Compared with earlier plain, flat sanitary napkins, a curved product with elasticized edges generally performs well, offering the advantage, for example, of greater comfort and security. The side edges tend to form a natural curve to better fit the body and a barrier to help prevent side leakage of menstrual fluids. However, in some applications there may be a tendency for the raised side edges to collapse against, or to fold in on top of, the absorbent element thereby allowing the panty elastic to be exposed. Thus, such a side edge no longer functions properly, and there may be leakage and staining of the panty as well as discomfort for the user.

Another form of conventional sanitary napkin, a flat pad with garment attachment panels (wings or flaps), potentially offers some of the same functional improvements and advantages over a plain pad as does the curved product with raised side edges. Typically, the form of this product before use is a flat pad with a pair of opposite garment attachment panels extending laterally outward from an absorbent element. The panels can be formed out of the cover and the baffle. In use, the absorbent element overlays the crotch portion of the panty in the normal way, and the panels are folded under to encircle the crotch portion. The panels may be secured beneath the panty to each other and/or to the panty crotch portion by suitable adhesive or mechanical fasteners. In use, the relative lateral disposition of the point at which each panel is folded (line of fold) is determined substantially by the user in a somewhat random fashion. Between users, or successive applications by a single user, there may be substantial variation in "fit" and working configuration with respect to the spacing of the fold in the panel from the edge of the absorbent and with respect to the disposition of the panty elastic relative to the edge of the absorbent and to the fold. Performance of the sanitary napkin may vary accordingly.

The garment attachment panels on flat conventional pads typically are designed to wrap around or fold over the panty elastic and form an upward element that fits into the groin of the wearer. Typically, the panels are nonabsorbent or minimally absorbent. This arrangement places additional nonabsorbent material in the crotch region, and during use the added material has a tendency to fold over onto the absorbent element. For the comfort and protection of an appropriate fit in the groin, the user is dependent on appropriate disposition and behavior of the panty elastic.

Van Tilburg (U.S. Pat. Nos. 4,589,876 and 4,687,478) and Mattingly (U.S. Pat. No. 4,608,047) disclose variations on and potential improvements over the general form of a flat pad with garment attachment panels referred to above.

The disclosures of the two Van Tilburg patents are substantially similar. They show a flat pad with laterally extending panels which fold over the panty elastic at the edge of the crotch portion but do not encircle the crotch portion. Each panel has two substantially parallel "lines of juncture" which provide "axes of flexibility." The axes of flexibility determine where each panel folds upward, in relation to the absorbent edge, and downward over the elastic edge of the panty. In use, it is intended that the panty elastic is pulled up into the groin so that the panel, enfolded about it, lies against the respective laterally, outward-facing surface of the labia majora. This forms a dam against lateral fluid flow and prevents side leakage. However, the desired configuration is not easily obtained in practice. Because the panty elastic is allowed to go up into the groin, the panels must be of sufficient length to cover the panty elastic throughout the length of the labia majora. Making the panels long can create a problem in that the end portions of the panels, toward the front and back of the pad, which have been folded around the panty crotch, are "fighting" with the panty elastic which is flaring out and cupping to the body. This can result in discomfort for the user and can cause the panels to come loose from the panty during wear. When the panels come loose, the panty elastic will tend to push the panels up onto the absorbent.

The napkin design taught by Mattingly is essentially that described above, for a conventional flat pad with garment attachment panels, but the disclosure is directed particularly to the "drapability" or sufficient flexibility of the panels. This drapability permits the panels to be folded at any lateral point to match the width of the panty crotch portion and avoid wrinkling. The panels may be of sufficient length to encircle the crotch portion and adhere to each other or to the panty. Mattingly recognizes the problem of the tendency of the panty crotch edge "to enfold onto the body facing surface of the napkin" but suggests allowing the folded panel configuration to be determined by panty crotch width rather than providing positive control of the juxtaposition of the panty elastic with the absorbent element edge.

The disclosures of McCoy (U.S. Pat. No. 4,900,320), Salerno (U.S. Pat. No. 4,940,462) and Seidy (U.S. Pat. No. 5,125,918) depart substantially from conventional flat pads with garment attachment panels described above. In that form, and before use, the panels are essentially lateral extensions of the cover and/or baffle surfaces of the pad. In McCoy, separate panels are affixed beneath the absorbent element, each at a point inward from the longitudinal edge of the absorbent element. This enables the panels to be folded around the crotch portion of the panty, gathering the panty under the absorbent element and removing its edges from proximity with the edges of the absorbent element and the possibility of becoming wet or stained. The attachment of the panels inward of the absorbent risks gathering the panty crotch so much that the user feels some discomfort. The narrower the pad and the wider the panty crotch, the more likely this is to occur. If the absorbent is made wider to avoid this problem, users with narrow crotch widths will experience some discomfort.

In Salerno, the garment attachment panels, which may comprise extensions of the cover or baffle portions of the sanitary napkin, are longitudinally expandable. Such panels, folded over a side of the crotch portion of an undergarment, may more readily conform to the contour of the undergarment and provide lateral protection without bunching of the undergarment. However, Salerno does not suggest use of the garment attachment panels to control lateral disposition of the undergarment crotch portion edge and, particularly, not of an elasticized edge in relation to an absorbent element in such a way as to prevent the elasticized edge from pulling in on top of the absorbent. Salerno's design does not particularly limit the disposition of the garment attachment panels when secured. They do not overlap and fasten together to establish a predetermined configuration when in use.

In Seidy, the garment attachment panels are truncated and supported at the opposite lateral edges of the absorbent element, extending inwardly and somewhat stiffly in a prefolded, flexible position. This enables the panty crotch portion to be maneuvered into position under the absorbent element and retained by the panels without the need for additional attachment adhesive.

As with Mattingly, the McCoy, Salerno and Seidy patents are concerned primarily with various aspects of treatment of the panty crotch portion in relation to the sanitary napkin. Mattingly teaches the avoidance of wrinkling, McCoy teaches a particular approach to shielding the crotch portion from wetting and staining, Salerno teaches side protection along the entire longitudinal edges of the napkin without bunching of the undergarment, and Seidy teaches the provision of panty edge shielding flaps without requiring additional attachment adhesive. None of these references suggest making use of garment attachment panels to enhance directly the performance of a sanitary napkin as a whole.

SUMMARY OF THE INVENTION

It is an object of this invention to provide a sanitary napkin which retains the functional characteristics and advantages of a curved, cup-shaped configuration. The napkin has functional side edges along its lateral sides and is enhanced by the inclusion of specific means for providing additional control of the functional side edges.

This object may be achieved in a sanitary napkin which includes an elongated absorbent pad, normally curved upward and having opposite longitudinal side edges which are deflectable with respect to a central portion of the pad. The pad includes an absorbent contained between a liquid-permeable cover and a liquid-impermeable baffle and may include a tension mechanism for inducing the upward curve of the pad. The pad also contains a control mechanism secured adjacent to the side edges for selectively controlling the deflection of the side edges so as to optimize the function of the sanitary napkin.

The control mechanism may comprise at least one garment attachment panel, normally extending generally downward and inward from its attachment at or adjacent to one of the deflectable side edges. In use, the garment attachment panel is anchorable under the crotch portion of an undergarment so as to confine the crotch portion and substantially define its lateral disposition relative to the pad and, particularly, to the absorbent element of the pad.

The garment attachment panel may include a fixed portion attached to the underside of the pad at one of the side edges and a free portion extending from the fixed portion and diverging from the underside of the pad. In use, the garment attachment panel extends under the crotch portion of the undergarment. The lateral disposition of the fixed portion of the panel, with respect to the pad, may define an outer lateral limit of disposition for a side edge of the crotch portion of an undergarment, particularly an elasticized side edge.

A fastening mechanism for connecting the opposite members of a pair of panels is preferably arranged so as to provide only a limited range of predetermined configurations with respect to deflection of the deflectable side edges and of the side edges of the absorbent with respect to its longitudinal center.

An advantage of the present sanitary napkin over conventional sanitary napkins with garment attachment panels, is that the disposition of the panty elastic edge is positively controlled. For example, the panty can be held under the absorbent and be prevented from folding up and over it. Furthermore, the present design helps the user avoid inadvertently folding a panel about the panty elastic thereby leaving the panty elastic free to pull the panel itself up into the groin and resulting in an undesirable "fit." The provided control of the panty elastic also prevents it from overlapping the functional or raised edges of the pad and pulling it on top of the absorbent.

Thus, the present sanitary napkin allows the functional characteristics and advantages of a curved sanitary napkin with functional or raised side edges to be preserved. Simultaneously, it permits a garment attachment panel to more reliably realize its potential for shielding and protecting the crotch portion of an undergarment.

A further object of the present invention is to provide a sanitary napkin having functional or raised side edges which can be controlled or pulled down, by the anchoring of a pair of garment attachment panels, to "gasket" comfortably against the thigh.

Another object of the invention is to provide a sanitary napkin in which, during use, the raised side edges of the pad remain free to function independently of the panty elastic.

Still another object of this invention is to provide a sanitary napkin in which the pull exerted on the raised side edges by a pair of garment attachment panels overcomes any tendency for the raised side edges to collapse onto or to fold in over the absorbent.

Still another object of the invention is to provide a sanitary napkin in which the garment attachment panels help to bias the pad convexly upward, conforming the pad to the body.

Yet another object of this invention is to provide a sanitary napkin in which control of the lateral disposition of the edge of the crotch portion of the undergarment results from the disposition of the effective attachment point of a garment attachment panel.

Still another object of the present invention is to provide a sanitary napkin configured so that, during use, the panty elastic is maintained beneath the absorbent and, at most, no higher than at the lateral side of the absorbent.

Other aspects of the invention and its scope will become apparent from the following description and the appended claims.

BRIEF DESCRIPTION OF THE DRAWINGS

FIG. 1 is a perspective view of a sanitary napkin according to the invention showing the curved form the pad may assume free of restraint, before installation, and with a pair of garment attachment panels extending downward.

FIG. 2 is a bottom view of the sanitary napkin shown in FIG. 1 with the garment attachment panels closed, and omitting adhesive 30 and peal strip/release paper 32.

FIG. 3 is a cross-sectional view of FIG. 2 taken along line 3—3.

FIG. 4 is a top view of the sanitary napkin shown in FIG. 1 with the garment attachment panels spread open as they might be before installation.

DESCRIPTION OF THE PREFERRED EMBODIMENTS

Referring to FIGS. 1–5, a sanitary napkin 10 is shown which represents an exemplary embodiment of the invention. It comprises a curved elongated absorbent pad 12 and a pair of garment attachment panels 14 and 16.

The form and construction of the absorbent pad 12 will be briefly described. It may be similar in form and share many details of construction with the absorbent pads disclosed in U.S. Pat. Nos. 4,701,177 and 4,770,657, both to Ellis et al. and assigned to Kimberly-Clark Corporation. These two patents are incorporated by reference and made a part hereof.

Figure 5:
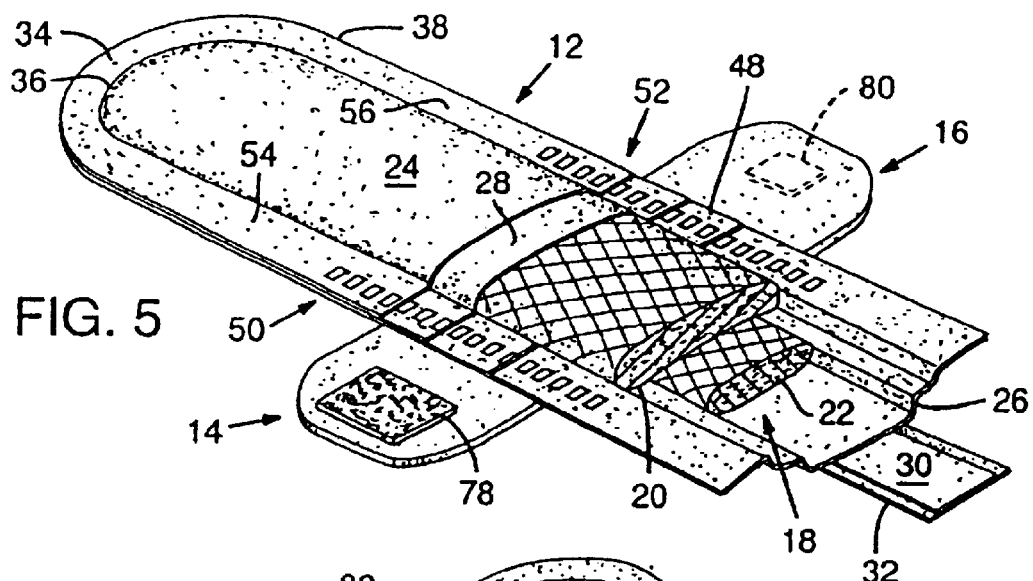
FIG. 5 is a partial schematic, cutaway perspective view (shown flat for clarity of presentation) of a sanitary napkin similar to that shown in FIG. 1 detailing its construction, and also showing an optional layer of tissue 28.

The absorbent pad 12 includes an absorbent 18 having two parts, both of which can be made from fluff. The two parts can include a bodyside absorbent portion 20 having a "race track" shape and a narrower, baffle side absorbent portion 22, in the form of a straight sided hump, which is narrower than the bodyside portion 20. The absorbent 18 is enclosed between a liquid-permeable cover 24 and a liquid-impermeable baffle 26. There may be a layer of tissue 28 between a the cover 24 and the absorbent portion 20 as shown in FIG. 5. The baffle 26 may carry a longitudinally central strip of garment adhesive 30 covered before use by a conventional, removable peel strip or release paper 32, as shown in FIGS. 1 and 5.

The cover 24 and the baffle 26 extend beyond the absorbent 18 and are bonded together to form a fringe 34 extending outward from a seal line 36 which closely borders the absorbent 18 and terminates at an outer peripheral edge 38. The edge seal 34 boarders along the longitudinal sides of the pad 12 to define opposite longitudinal side edges 40 and 42 and extending generally outward from and adjacent to longitudinal side edges 44 and 46 of the absorbent 18. In the longitudinally central portion of the pad 12, and within the longitudinal side edges 40 and 42 are positioned elongated elastic strips 48. The elastic strips 48 are incorporated under tension so that, when they are allowed to relax, the tension gathers and elevates each longitudinal side edge portion to define a pair of oppositely aligned elasticized raised side edges 50 and 52. The raised edges 50 and 52 (shown raised in FIGS. 1 and 2, but shown flat in FIG. 5 for clarity of presentation and to better illustrate the structure) have inner and outer walls 54, 56, 58 and 60, respectively, formed by the respective extensions of the cover 24 and the baffle 26.

Figure 8:
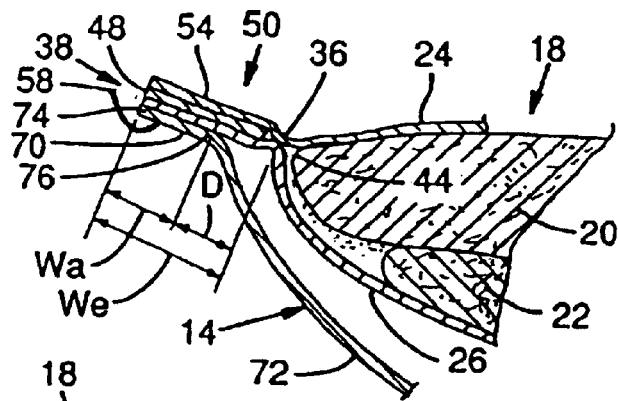
FIG. 8 is an enlarged partial schematic cross-sectional view of the sanitary napkin shown in FIG. 1 depicting the attached relationship of a garment attachment panel to an elasticized raised edge.

The garment attachment panels 14 and 16 are identical to one another apart from the anchoring elements they carry, and therefore only one will be described. The garment attachment panel 14 consists of a generally rectangular sheet of material which, in assembly, has a fixed or attachment portion 70 and a free portion 72 which is best shown in FIG. 8. The fixed portion 70 overlays and is bonded to the outer wall 58 of the elasticized raised side edge 50. The attachment area extends from an outer edge 74, located adjacent to the peripheral edge 38, to an inner edge or effective point of attachment 76. The effective point of attachment is equivalent to the lateral limit of the garment attachment panel. The free portion 72 of the garment attachment panel 14 diverges from or hinges at the effective point of attachment 76. The fixed portion 70 of the garment attachment panel 14 is presented to the outer wall 58 of the elasticized raised side edge 50 so that it shares in the gathering of the side edge 50. The free portion 72 of the garment attachment panel 14 becomes somewhat concave to the underside of the pad 12 when it assumes its curved form. The elevation of the elasticized raised side edges 50 and 52 directs the free portion 72 of the garment attachment panels 14 and 16 generally downward and inward.

The free portions of the garment attachment panels 14 and 16 are provided with means for anchoring the free portions of the garment attachment panels 14 and 16 so as to establish a predetermined deflection of the absorbent pad side edges, causing a predetermined particular confinement of the side edges of the crotch portion of the undergarment, and so as to facilitate accurate mounting of the sanitary napkin on the undergarment which comprise mating fastener elements 78 and 80 secured to the garment attachment panels 14 and 16, which mating fastener elements are configured so as to provide substantially only a single predetermined lateral relation of one garment attachment panel to the other. The anchoring elements 78 and 80 include a mechanical fastener of conventional hook and loop type fabric. A relatively small patch 78 of loop material is attached to the garment attachment panel 14, and a smaller patch 80 of hook material is attached to the garment attachment panel 16. The anchoring elements 78 and 80 are located so that the garment attachment panels 14 and 16 may be anchored together under the absorbent 18 as is shown in FIG. 3. This invention may be practiced successfully with pads having a wide range of sizes and proportions as indicated in the following exemplary Table 1.

TABLE 1

| DIMENSIONS (inches): | Nominal | Range | Preferred Range |
|---|---|---|---|
| Pad 12: Length (unstretched) | 9.0 | 7.0–13.0 | 8.0–11.0 |
| Length (stretched) | 10.0 | 8.0–14.0 | 9.0–12.0 |
| Width | 3.5 | 2.0–4.5 | 2.5–4.0 |
| Panel 14 and 16: | | | |
| Length | 2.0 | 1.0–5.0 | 1.5–3.0 |
| Width | 2.25 | 1.5–2.75 | 1.75–2.5 |
| Attachment Width (Wa) | 0.25 | 0.125–0.5 | 0.125–0.5 |

With reference to FIG. 1, exemplary ranges of size dimensions in inches for the loop and hook fastener elements 78 and 80 are as follows:

TABLE 2

| | Range | Preferred Range |
|---|---|---|
| Hook element 80 - Width Wh | 0.25–1.0 | 0.25–0.5 |
| Loop element 78 - Width Wl | 0.25–1.5 | 0.5–1.0 |
| Hook element 80 - Length Lh | 0.25–3.0 | 0.25–1.5 |
| Loop element 78 - Length Ll | 0.25–3.0 | 0.5–1.5 |

The scope of this invention also permits the use of a variety of materials as well as variations in configuration. In the absorbent pad 12, on which the garment attachment panels 14 and 16 are mounted, variations may include different methods of obtaining the curvature of the pad 12 and elevating the raised side edges 50 and 52. Other pad outline shapes are also possible, such as barrel, rectangular or hourglass. In alternative designs, the absorbent 18 could extend into the raised side edges 50 and 52.

As for alternative material, the elastic strips 48 in the elasticized raised edges 50 and 52 may be made from one of the natural rubbers, from a KRATON (styrenic block polymer based on styrene, butadiene and isoprene)-based thermoplastic elastomer, or from one of the polyurethanes. Suitable materials for the garment attachment panels 14 and 16 include polymeric films, nonwovens, elastomerics, or composites of these materials.

With regard to the anchoring elements 78 and 80 for the garment attachment panels 14 and 16, alternative mechanical fasteners work well. Adhesive fastening may also be used, but the potential precision of a mechanical fastener is preferred as will be discussed further below.

Figure 6:
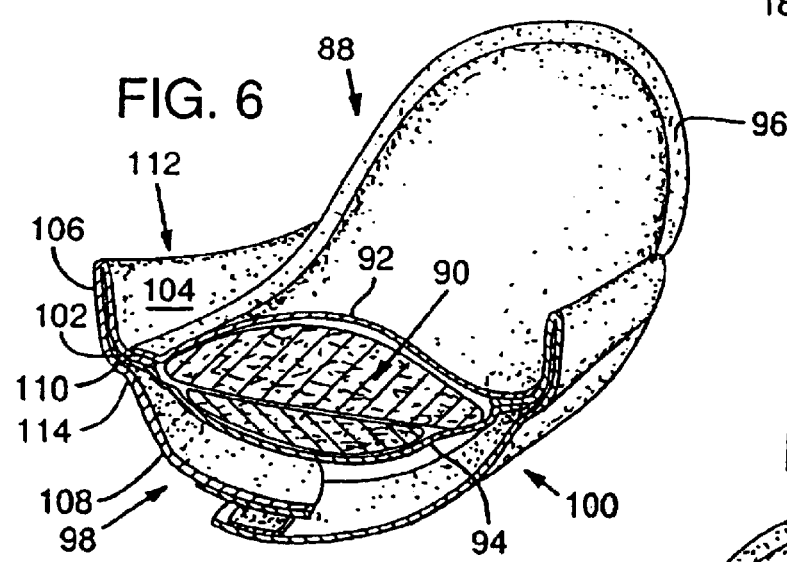
FIG. 6 is a cross-sectional view of an alternative embodiment of a sanitary napkin showing garment attachment panels integrally formed with the elasticized raised edges of the napkin.
Figure 7:
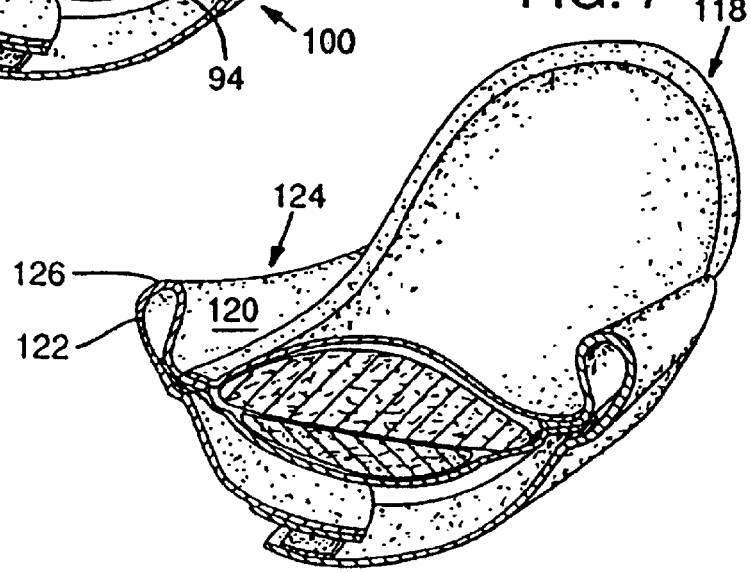
FIG. 7 is a cross-sectional view of a second alternative embodiment of a sanitary napkin.

Referring to FIGS. 6 and 7, alternative embodiments of the garment attachment panels are shown wherein they are formed integral with the raised side edges of absorbent pad 88. The pad 88 includes a two-part absorbent 90 enclosed by a cover 92 and a baffle 94. Both the cover 92 and the baffle 94 extend beyond the periphery of the absorbent 90 to form a fringe 96. The pad 88 further includes two garment attachment panels 98 and 100 which are similar, and therefore only one will be described. In the garment attachment panel 98, a narrow inner edge portion 102 is bonded between the edges of the cover 92 and the baffle 94. The garment attachment panel 98 extends outward and upward and is folded back on itself to define sealed inner and outer walls 104 and 106. The garment attachment panel 98 ends in a depending free portion 108. The garment attachment cover 92, the panel 98, the inner edge 102, the baffle 94, construction adhesive 110, and the base of the outer wall 106 are all bonded together to establish an elasticized raised side edge 112. The raised edge 112 and the panel 98 are of the same material, which may be elastic. Other means may also be used to impart curvature to the pad. The inner edge of the bonding or sealing of the materials at the edge of the pad establishes an effective attachment point 114 from which the free or functional portion 108 of the garment attachment panel 98 depends or is hinged. Thus, in this embodiment, and similarly in that of FIG. 7, the inner and outer walls 104 and 106 of the elasticized raised side edge 112 and the garment attachment panel 98 are formed from a single sheet of material.

Referring to FIG. 7, an absorbent pad 118 is shown which is similar to that of FIG. 6 except that inner and outer walls 120 and 122, which form part of an elasticized raised side edge 124, are not completely sealed together. This enables the upper portion of the raised side edge 124 to form a soft rolled edge 126.

There are many suitable alternative arrangements for making the juncture between the absorbent pad and the garment attachment panel. Preferably, any arrangement should provide an "effective attachment point" on the underside of the raised edge and inset from its outer periphery as exemplified at 76 and 114 above. See particularly FIGS. 6 and 8. The garment attachment panel may, for example, be formed from an extension of the cover and/or the baffle of the absorbent pad. It may be a separate piece of material wrapped over the raised edges 50 and 52 with the free portion 108 of the panel 98 diverging from the underside of the raised edge 112. The fixed portion 70 of the panel 14 may be bonded between the layered components of the raised edge 50. The material forming the garment attachment panel 14 emerges to fold downward and inward under the pad 12.

Figure 11:
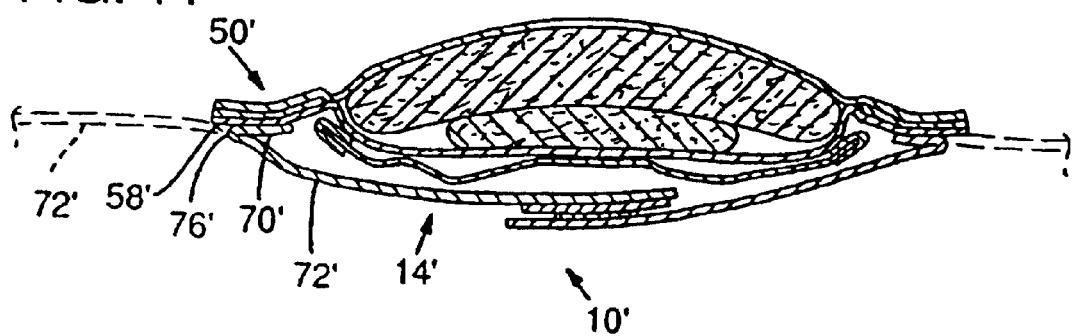
FIG. 11 is a cross-sectional view of a sanitary napkin showing an alternative embodiment for attaching the garment attachment panels to an elasticized raised edge.

Another example is shown in FIG. 11, wherein a sanitary napkin 10' is illustrated. Here, compared with the first embodiment shown in FIG. 8, the attachment configuration for a garment attachment panel 14' has been reversed. A fixed portion 70' of the panel 14' has been laid on an underside or outer wall 58' of a normally raised edge 50' with the panel 14' initially directed outward. In use, a free portion 72' of panel 14', the position of which when unfolded is shown in broken line in the leftmost portion of FIG. 11, is folded back under the raised edge 50' at an effective attachment point 76'.

The modes of using, and performance characteristics of all embodiments of the invention disclosed herein, are similar and will be described with reference to the first embodiment shown in FIGS. 1–5 and with particular reference to FIGS. 9, 10, and 11.

In preparation for use, the peel strip 32 is removed from the pad 12 exposing the garment attachment adhesive 30. With the garment attachment panels 14 and 16 spread apart, the pad 12 is centered and mounted onto a crotch portion of an undergarment in the usual way. After the crotch portion 130 of the undergarment is uniformly distributed over the garment-facing side, or underside, of the baffle 26, the garment attachment panels 14 and 16 are closed by bringing together the anchoring elements 78 and 80. As seen in the drawings, the anchoring elements 78 and 80 are relatively small. In fastening the garment attachment panels 14 and 16, the degree of overlap of the anchoring elements 78 and 80 may vary. This provides some adjustability or variation in the tightness or snugness with which the garment attachment panels 14 and 16 are fastened, and a user may choose to make some individual use of this factor. However, the range of adjustment is intentionally limited. The range provided in a given pad is large enough to make it easy for the user to install the product but small enough to ensure that it is always installed so that it will function as intended. Some preferred ranges of adjustment are indicated in the above Table 2. The range of lateral adjustment is determined by the corresponding width dimensions Wl of the loop element 78 and Wh of the hook element 80. Normally, the garment attachment panels 14 and 16 are fastened so that the anchoring elements 78 and 80 are approximately centered one on the other as indicated in FIGS. 9 and 10. The configuration of the sanitary napkin 10, including the range of adjustment provided for the anchoring elements 78 and 80, is such that, when the garment attachment panels 14 and 16 are properly fastened, the crotch portion 130 of the undergarment is always confined beneath the pad 12. This enables the edge of the crotch portion 130 and the panty leg elastic 132 to be disposed laterally no further out than the edge of the absorbent 18 or certainly no higher than its lateral sides. See FIGS. 9 and 10.

The limit of lateral disposition of the panty elastic 132 is determined by the "stop" provided at the effective attachment point 76 of the respective garment attachment panels 14 and 16. The chosen location for the effective attachment point 76 is important to the function of the sanitary napkin 10. If it is too low on the elasticized raised side edges 50 and 52, and hence too close to the longitudinal side edges 44 and 46 of the absorbent 18 and to the seal line 36, any pull or tension set up in the garment attachment panels 14 and 16 when they are fastened will have relatively little effect in controlling the elasticized raised side edges 50 and 52. If the effective attachment point 76 is too high or too far out on the elasticized raised side edges 50 and 52, the pull of the garment attachment panels 14 and 16, when fastened, may force the elasticized raised side edges 50 and 52 down so far as to reduce its effectiveness.

Referring to FIG. 8, the effective width (We) of each of the elasticized raised side edges 50 and 52 is in the range of about 0.25 to about 1 inch. A preferred range of widths (Wa) for the fixed attachment portion 70 of each of the garment attachment panels 14 and 16 is from about 0.125 to about 0.5 inches. A preferred spacing (D) between the effective point of attachment 76 and the absorbent side edges 44 and 46 is in the range of about one third to three quarters of the width (We) of the elasticized raised side edges 50 and 52.

When the panty elastic is shielded by controlling its position, as in the present invention, rather than by simply covering it with a long garment attachment panel, as in Van Tilburg for example, a shorter garment attachment panel may be used effectively. See the preferred range of panel lengths of about 1.5" to about 3.0" in Table 1. With shorter panels, the possible discomfort of longer panels and inconvenience of their "popping open" is avoided.

Another advantage of the present invention is that the curvature of the raised side edges 50 and 52 allows the garment attachment panels 14 and 16 to stay outward, or open, in positions intermediate those shown in FIGS. 1 and 4, for example, when the user is positioning the pad 12 in the undergarment. This avoids the problem of the panels 14 and 16 getting caught under the pad 12 which sometimes occurs in conventional flat pads with garment attachment panels.

Figure 9:
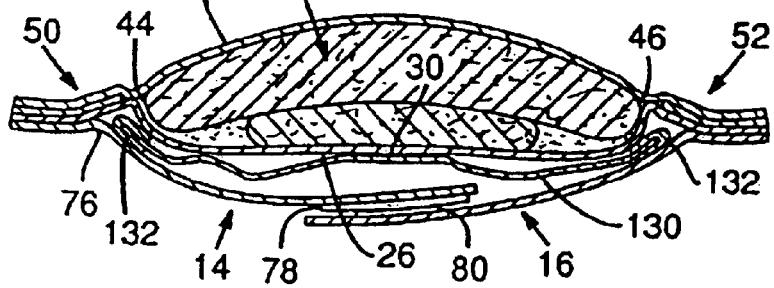
FIG. 9 is a cross-sectional view of the sanitary napkin shown in FIG. 1 mounted onto the crotch portion of an undergarment before contact with the wearer's body.

Returning to preparations for use of the sanitary napkin 10, an exemplary configuration of the sanitary napkin 10 mounted on an undergarment, and before being worn, is shown in FIG. 9. With the garment attachment panels 14 and 16 properly fastened, the elasticized side edges 50 and 52 are pulled down so that the absorbent 18 arches convexly upward. Note that the anchoring elements 78 and 80 are approximately centered one on the other.

Figure 10:
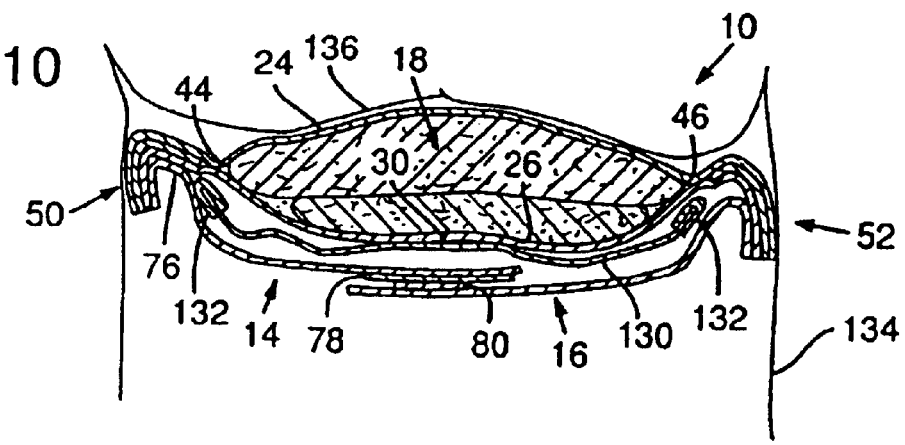
FIG. 10 is a cross-sectional view of the sanitary napkin shown in FIG. 1 as worn by a female with the elastic raised edges of the sanitary napkin folded down and gasketing the thighs.

Referring to FIG. 10, a sanitary napkin is shown during use. The elasticized raised side edges 50 and 52 are partially folded, "gasketing" comfortably against the wearer's thigh 134. The upwardly convex form of the absorbent 18 fits more closely to the source of the menstrual flow and more comfortably against the wearer's labia majora 136.

Important aspects of the invention are control of the deflectable side edges 50, 52, 112 and 124 of the absorbent pad 12 and control of the elastic edges 132 of the crotch portion 130 of an undergarment.

As discussed above, fastening the garment attachment panels 14 and 16 helps configure the pad for effective use. In addition, when they are properly fastened, the downward pull of the garment attachment panels 14 and 16 on the elasticized raised side edges 50 and 52 prevents the raised edges of the pad 12 from collapsing against or folding in on top of the absorbent 18 during preparation for or during use.

The key to the control of the elastic edges 132 of the crotch portion 130 of the undergarment is the disposition during use of the effective attachment point 76 of each of the garment attachment panels 14 and 16. The disposition of the attachment points 76 establishes a limit or stop for lateral disposition of the panty elastic 132. Preferably, and as shown in FIG. 10, the panty elastic 132 is confined to be under the absorbent side edges 44 and 46 or no higher than along side the absorbent 18. This control prevents the panty elastic 132 from pulling in onto the top of the absorbent 18. It also ensures that the elasticized raised side edges 50 and 52 remain independent of biasing by the panty elastic 132. Another positive result of panty elastic disposition control is that, with the panty elastic 132 held under the absorbent side edges 44 and 46, the panty elastic 132 may help to bias the absorbent 18 upward for a better fit to the body. Still another advantage is that the configuration of the sanitary napkin 10, and particularly that of the garment attachment panels 14 and 16, is such that, in preparation for use, a user cannot inadvertently fold and fasten the garment attachment panels 14 and 16 over the panty elastic 132. This prevents the panty elastic 132 from pulling either of the garment attachment panels 14 and 16 up into the groin.

The present invention allows the functional characteristics and advantages of a curved sanitary napkin 10 with elasticized raised side edges 50 and 52 to be preserved while at the same time permitting the garment attachment panels 14 and 16 to more reliably realize their potential for shielding and protection of the crotch portion 130 of an undergarment.

While the invention has been described in conjunction with several specific embodiments, it is to be understood that many alternatives, modifications, and variations will be apparent to those skilled in the art in light of the aforegoing description. Accordingly, this invention is intended to embrace all such alternatives, modifications, and variations which fall within the spirit and scope of the appended claims.

We claim:

1. A sanitary napkin for mounting onto a bodyside of a crotch portion of an undergarment, and, during use, absorbing bodily excretions, comprising:

an elongated absorbent pad having a longitudinal axis, a longitudinally central portion and opposite longitudinal side edges, said pad side edges being deflectable with respect to said central portion, and including an absorbent having longitudinal side edges and being contained between a body-faceable side, liquid-permeable cover and a garment-faceable side, liquid-impermeable baffle, said absorbent pad being normally curved upward with respect to its longitudinal axis; and control means for selectively controlling deflection of at least one of said pad side edges during use, said control means being anchorable under said crotch portion of said undergarment, said anchoring at least potentially establishing a generally downward pull on said pad side edge and preventing said pad side edge from folding in towards said absorbent pad, wherein said control means comprises two garment attachment panels, normally extending, respectively, generally downward and inward from said absorbent pad adjacent to said pad side edges and wherein said garment attachment panels each include a fixed portion attached to the underside of said absorbent pad towards the adjacent Dad side edge and defining a garment attachment point and a free portion diverging from the underside of said absorbent pad for, during use, extending under said crotch portion of said undergarment, and including means for anchoring said free portions of said garment attachment panels to establish a predetermined deflection of at least one of said pad side edges and to facilitate accurate mounting of said sanitary napkin on said undergarment.

2. A sanitary napkin for mounting onto the bodyside of a crotch portion of an undergarment, and, during use, absorbing bodily excretions, comprising:

an elongated absorbent pad having a longitudinal axis, a longitudinally central portion and opposite longitudinal side edges, said pad side edges being deflectable with respect to said central portion, and including an absorbent contained between a bodyside, liquid-permeable cover and a garment side, liquid-impermeable baffle, said absorbent pad being normally curved upward with respect to its longitudinal axis; and control means for selectively controlling deflection of said pad side edges during use, said control means being anchorable under said crotch portion of said undergarment, said anchoring establishing a generally downward pull on said pad side edges and preventing said pad side edge from folding in toward said absorbent pad wherein said control means comprises first and second opposite garment attachment panels, normally extending, respectively, generally downward and inward from said absorbent pad adjacent to said pad side edges and wherein said garment attachment panels each include a fixed portion attached to the underside of said absorbent pad towards the adjacent pad side edge and a free portion diverging from the underside of said absorbent pad for, during use, extending under said crotch portion of said undergarment, wherein a garment attachment point is defined where said fixed and said free portions meet each other; and including means for anchoring said free portions of said garment attachment panels so as to establish a predetermined deflection of said absorbent pad side edges, causing a predetermined particular confinement of said pad side edges of said crotch portion of said undergarment, and so as to facilitate accurate mounting of said sanitary napkin on said undergarment, and wherein said means for anchoring said free portions of said garment attachment panels comprises mating fastener elements, one on each of said garment attachment panels, said fastener elements being configured as to provide substantially only a single predetermined lateral relation of one garment attachment panel to the other.

3. The sanitary napkin of claim 2, wherein the predetermined deflection of said pad side edges and the predetermined particular confinement of said pad side edges of said crotch portion of said undergarment biases said absorbent pad into an upwardly convex form, for closely fitting a body.

4. The sanitary napkin of claim 2, wherein during use, the anchoring of said garment attachment panel configures said sanitary napkin so that each side edge of said crotch portion of said undergarment is supported approximately no higher than said side edges of said absorbent pad.

5. The sanitary napkin of claim 2, wherein the lateral disposition of said fixed portions of said garment attachment panels and the anchoring of said garment attachment panels configure said sanitary napkin so that, during use, each side edge of said crotch portion of said undergarment is supported approximately beneath an adjacent side edge of said absorbent pad and said absorbent pad is free to conform to a body of a user.

6. The sanitary napkin of claim 2, wherein said fixed portions of said garment attachment panels are disposed so that, during use, each side of said crotch portion of said undergarment is restrained adjacent to an adjacent side edge of said absorbent pad and prevented from overlaying said absorbent pad.

7. The sanitary napkin of claim 2, wherein said side edges of said absorbent pad have a lateral periphery and said absorbent pad has longitudinally extending lateral sides contiguous with said pad side edges, respectively, and each garment attachment point of said garment attachment panels has an inner lateral limit, the inner lateral limit of the garment attachment point of one panel being disposed between an adjacent one of said lateral sides of said absorbent pad and the lateral periphery of the side edge of said pad adjacent thereto.

8. The sanitary napkin of claim 2, wherein said cover and said baffle extend laterally beyond said absorbent to define said pad side edges and wherein said garment attachment panels are secured to said baffle outwardly of said absorbent.

9. The sanitary napkin of claim 2, wherein the side edges of the absorbent pad, the cover and the baffle are bonded together to form an edge seal.

10. The sanitary napkin of claim 9, wherein the garment attachment panels are attached to the baffle side of the edge seal.

11. The sanitary napkin of claim 2, wherein at least one of the cover and the baffle extend laterally beyond the absorbent to define said pad side edges.

* * * * *